(12) United States Patent
Palmer

(10) Patent No.: US 8,361,520 B2
(45) Date of Patent: Jan. 29, 2013

(54) ANTIOXIDANT SKIN CARE COMPOSITIONS

(76) Inventor: Debbie M. Palmer, Greenwich, CT (US)

( * ) Notice: Subject to any disclaimer, the term of this patent is extended or adjusted under 35 U.S.C. 154(b) by 141 days.

(21) Appl. No.: 12/900,637

(22) Filed: Oct. 8, 2010

(65) Prior Publication Data

US 2012/0087996 A1   Apr. 12, 2012

(51) Int. Cl.
*A61K 36/42* (2006.01)
*A61K 36/82* (2006.01)
*A61K 36/45* (2006.01)
*A61K 36/886* (2006.01)
*A61K 36/752* (2006.01)
*A61K 36/73* (2006.01)
*A61K 36/736* (2006.01)
*A61K 36/87* (2006.01)

(52) U.S. Cl. ........ 424/732; 424/744; 424/750; 424/766; 424/736; 424/765; 424/770; 424/729; 424/757; 424/758; 424/764; 514/458; 514/725; 514/474

(58) Field of Classification Search ........................ None
See application file for complete search history.

(56) References Cited

U.S. PATENT DOCUMENTS

2007/0065396 A1* 3/2007 Morariu .......................... 424/74
2009/0175973 A1* 7/2009 Vikhrieva ...................... 424/777

* cited by examiner

*Primary Examiner* — Susan Hoffman
(74) *Attorney, Agent, or Firm* — Nixon & Vanderhye

(57) ABSTRACT

Antioxidant skin care composition comprising at least two antioxidant components one of which is a solid coffee extract antioxidant, which exhibits a synergistically increased antioxidant potency as measured by ORACsc compared to the antioxidant potency of antioxidant skin care compositions which do not contain at least two antioxidant components one of which is a solid coffee extract antioxidant. The skin care compositions are particularly suited for use in the treatment of wrinkles, pigmentation effects caused by sun damage and redness in the skin.

4 Claims, No Drawings

ANTIOXIDANT SKIN CARE COMPOSITIONS

FIELD OF THE INVENTION

The present invention relates generally to the field of skin care compositions, methods of formulating same, and methods of using them. More particularly, the present invention provides antioxidant skin care compositions comprising at least two antioxidant components, one of which is a coffee extract antioxidant, for example *coffea arabica* extract, which possess unexpected beneficial effects.

BACKGROUND OF THE INVENTION

A free radical is defined as an atom or molecule with an unpaired electron. These unstable entities are chemically reactive and can harm the skin's DNA, RNA, proteins and lipids through oxidation.

Antioxidants protect cells by neutralizing free radical damage by donating an electron to unstable free radicals. It is now increasingly being realized that antioxidants can play an important role in the treatment and/or prevention of a number of diseases, including cancer, heart, vascular, and neurogenitive diseases.

A focus for the use of antioxidants is in the treatment of conditions of the skin. However, to date, no effective compositions have been developed. As a result, a need exists for improved antioxidant skin care compositions in order to reduce the damaging effects of free radicals. The present invention seeks to meet that need.

BRIEF DESCRIPTION OF THE INVENTION

The present invention provides an antioxidant skin care composition comprising at least two antioxidant components which together give rise to a synergy in their effect when used in the treatment of skin conditions. Thus, in a first embodiment, there is provided an antioxidant skin care composition comprising at least two antioxidant components which together generate a synergistic effect when used in treatment of skin conditions. One of the two components is preferably a coffee extract antioxidant, for example *coffea arabica* extract.

In further aspect, there is provided a process of preparing an antioxidant skin care composition, comprising formulating at least two antioxidant constituents, one of which is a coffee extract, employing a low heat process in which antioxidant constituents in solid form are formulated with other constituents at a low temperature, for example around room temperature, to avoid causing damage to the antioxidant components.

In yet a further embodiment of the invention, there is provided a method of treating skin conditions in a patient in need of such treatment, comprising administering to the patient a therapeutically effective amount of an antioxidant skin care composition of the invention. Typically, the composition is applied topically to the affected area of the skin.

DETAILED DESCRIPTION OF THE INVENTION

In a first embodiment, the present invention provides an antioxidant skin care composition comprising at least one coffee extract antioxidant, for example a *coffea arabica* extract, and at least one further antioxidant component. The coffee extract is preferably in solid form, typically in the form of solid particles. The at least on further antioxidant may be in solid or liquid form. When a liquid, the further antioxidant it is typically in the form of an oil.

The solid antioxidant is typically present in the compositions in an amount of 5-15 wt %, for example 8-12 wt %. The at least one further antioxidant, for example an oil, is typically present in an amount of 0.05-0.5 wt %.

It has been found, surprisingly, according to the invention, that the combination of a solid antioxidant constituent, including a coffee extract antioxidant, for example *coffea arabica* extract, and a further antioxidant in liquid or oil form, gives rise to a synergistic effect with respect to the antioxidant potency of the composition. The expression "synergistic effect" as used herein means that the antioxidant potency of the antioxidant compositions of the invention, as measured by the score obtained using the ORACsc testing protocol, is surprisingly increased as compared to the ORACsc scores of antioxidant compositions not containing a combination of a solid antioxidant constituent, including a coffee extract antioxidant, for example *coffea arabica* extract, and a further antioxidant in solid or liquid (oil) form.

The antioxidant skin care compositions of the invention typically have a pH in the range of 3.0 to 6.5, for example 4-6. The specific pH range will depend on the particular nature of the composition. Examples are discussed below.

The antioxidant skin care compositions of the invention typically have a viscosity in the range of T/C 20,000-65,000 cp5 rpm, for example 25,000-58,000 cp5 rpm. The specific viscosity range will depend on the particular nature of the composition. Examples are discussed below.

In a preferred embodiment, the antioxidant skin care composition of the invention comprises the following constituents in the recited wt. percentages: stabilized AV gel 38-44, xanthan gum 0.1-0.5, Carbopol 940 (cross-linked polyacrylate polymer) (2%) 5-15, Hydrolite-5 (pentylene glycol) 1-5, panthenol 0.1-0.5, glycerin 2-8, sodium PCA 0.2-0.9, tetrasodium EDTA 0.05-0.5, allantoin 0.1-0.5, Promulgen D (ethoxylated cetearyl alcohol compounded with cetaryl alcohol) 1-5, cetyl alcohol 1-5, stearic acid 1-5, Liponate GC (caprylic/capric triglyceride) 2-10, cyclomethicone 1-5, rice bran oil 0.05-0.5, avocado oil 0.05-0.5, Dimethicone 47V20 (polydimethylsiloxane) 1-4, olive oil 1-5, vitamin E 0.01-0.1, Simulgel NS (hydroxyethylacrylate/sodium acryloyldimethyl taurate copolymer & squalane & Polysorbate 60 the latter of which is polyoxyethylene (20) sorbitan monostearate) 1-5, Optiphen Plus (phenoxyethanol and caprylyl glycol and sorbic acid) 0.1-5, grape seed extract 0.05-0.5, VitaBerry (antioxidant blend of whole fruit powders and extracts combining wild blueberry, cranberry, raspberry, strawberry, prune, cherry, wild bilberry and grape) 0.05-0.5, quercetin 0.05-0.5, goji berry extract powder 0.1-0.5, coffee cherry extract powder or green coffee extract powder 5-15, vitamin A 0.01-0.1, vitamin C 0.05-0.1, hyasol 1-5, biotin 0.05.0.5, OPC pine bark 0.1-1.0, ACAI extract 0.05-0.5, guarana extract 0.5-5, green tea extract 0.05-0.5, licorice extract 0.05-0.5, cucumber extract 0.05-0.5, chamomile extract 0.05-0.5, tea 99% 0.01-1, grapefruit oil #1854 0.05-0.5, orange oil #1085 0.05-0.5, aromatic pomegranate extract #H2580 0.05-0.5, to a total of 100.00 wt %.

In further aspect, there is provided a process of preparing an antioxidant skin care composition, comprising formulating at least two antioxidant constituents, at least one of which is a solid antioxidant coffee extract, under low heat conditions such that the at least one solid antioxidant constituent is not subjected to a temperature which would adversely affect the antioxidant potency of the antioxidant. In such a low heat process, the temperature when the solid antioxidant(s) is admixed is typically maintained at about 20-45° C., for example 25-30° C., more usually around room temperature.

In one aspect, the process of the invention comprises heating a first phase comprising at least a stabilized gel in a first vessel to a temperature of 80° C. or less, heating a second phase comprising at least one antioxidant in the form of an oil in a separate vessel to a temperature of 80° C. or less, homogenizing the first and second phases to give a first homogenized phase at a temperature of 80° C. or less, homogenizing a third phase comprising a stabilizer with the first homogenized phase at a temperature of 80° C. or less to give a second homogenized phase, cooling the second homogenized phase to a temperature in the range of 20-45° C. to give a cooled phase, adding at least one solid antioxidant in powder form to the cooled phase at a temperature of 20-45° C. to give a final mixture, and homogenizing the final mixture at a temperature of 20-45° C. to give a skin care composition of the invention.

In one particular embodiment, the process comprises:

heating to a temperature of 80° C. or less in a first vessel a first phase (A) composed of the following constituents in wt. % amounts: stabilized AV gel 38-44, xanthan gum 0.1-0.5, carbopol 940 (2%) 5-15, hydrolite-5 1-5, panthenol 0.1-0.5, glycerin 2-8, sodium PCA 0.2-0.9, tetrasodium EDTA 0.05-0.5, and allantoin 0.1-0.5, heating to a temperature of 80° C. or less in a separate vessel a second phase (B) composed of the following constituents in wt % amounts: Promulgen D 1-5, cetyl alcohol 1-5, stearic acid 1-5, Liponate GC 2-10, cyclomethicone 1-5, rice bran oil 0.05-0.5, avocado oil 0.05-0.5, Dimethicone 47V20 1-4, olive oil 1-5, and vitamin E 0.01-0.1, homogenizing the first and second phases at a temperature of 80° C. or less to give a first homogenized phase, homogenizing a third phase (C) comprised of simulgel NS 1-5 wt % with the first homogenized phase at a temperature of 80° C. or less to give a second homogenized phase, cooling the second homogenized phase to a lower temperature, for example 20-45° C., to give a cooled phase, adding a phase (D) comprised of optiphen 0.1-5 wt % to the cooled phase at 20-45° C., and adding to the cooled phase at 20-45° C. a mixture of phases comprised of (E) grape seed extract 0.05-0.5, VitaBerry 0.05-0.5, quercetin 0.05-0.5, goji berry extract powder 0.1-0.5, coffee cherry extract powder or green coffee extract powder 5-15, (F) vitamin A 0.01-0.1, vitamin C 0.05-0.1, and hyasol 1-5, (G) biotin 0.05.0.5, (H) OPC pine bark 0.1-1.0, ACAI extract 0.05-0.5, guarana extract 0.5-5, green tea extract 0.05-0.5, licorice extract 0.05-0.5, cucumber extract 0.05-0.5, and chamomile extract 0.05-0.5, (I) tea 99% 0.01-1, and (J) grapefruit oil #1854 0.05-0.5, orange oil #1085 0.05-0.5, and aromatic pomegranate extract #H2580 0.05-0.5, to a total of 100.00 wt %.

Processing of the skin care formulation of the invention is carried out under low heat conditions to not adversely affect the antioxidant potency of the antioxidant constituents. This is achieved according to the process by ensuring that, when the solid antioxidant constituents are present in the formulation, the process is conducted under low heat conditions such that the temperature of the formulation is maintained in the range of about 20-45° C., more usually 25-30° C., for example around room temperature. In the particular embodiment described above, the low heat conditions are maintained while the phases E, F, G, H, I and J, in which the solid antioxidants are present, are mixed with the cooled homogenized mixture obtained by mixing phases A, B, C and D.

By controlling the input of heat while the solid antioxidant constituents are admixed with the phase containing the liquid (oil) antioxidant(s), it has been found according to the invention, that the antioxidant potency of the compositions is surprisingly increased as compared to the antioxidant potency of the respective individual antioxidant constituents. This observation evidences the presence of an unexpected synergistic effect with regard to the antioxidant potency of the combination of antioxidants, not observed with the individual antioxidants.

Three sample formulations have been produced according to the present invention, namely an eye serum, a night crème and a day lotion. The ORACsc (oxygen radical absorbance capacity—skin care) has been determined for these formulations. The scores obtained using the ORACsc testing method is a measure of the capability of an antioxidant serum, crème or lotion to absorb free radicals, i.e., the antioxidant potency of the composition.

The formulations of the invention produced surprisingly high ORACsc scores (micromole TE/100 g). The eye serum crème ORACsc score was 79,507; the night crème ORACsc score was 49,321 and the day lotion ORACsc score was 18,506.

Skin conditions which may be treated using the compositions of the invention include, but are not limited to, the presence of wrinkles, pigmentation effects caused by sun damage and redness in the skin. The compositions have been found to be particularly effective in treating the presence of wrinkles, lack of skin firmness, hyper-pigmentation, blotchy redness and tactile roughness in photo-damaged skin.

The antioxidant skin care compositions are typically formulated for topical application, and are usually in the form of a serum, crème or lotion. The antioxidant skin care composition containing the percentage ranges defined above is typically applied to affected areas of the skin in a therapeutically effective amount, that is an amount which produces an advantageous effect by reducing and/or eliminating the condition present on the affected area of the skin as compared to the outcome of not treating the affected skin area. Typically, the amount of the composition, as defined about in terms of percentage amounts applied to the affected skin area, approximates the size of a dime. The serum, crème or lotion is usually applied over the affected skin area until evenly distributed.

EXAMPLES

Example 1

Lighten & Firm Eye Serum

| Phase | Constituents | Wt. Percent |
|---|---|---|
| A | STABILIZED AV GEL | 42.990 |
|  | XANTHAN GUM | 0.300 |
|  | CARBOPOL 940 (2%) | 10.000 |
|  | HYDROLITE-5 | 2.000 |
|  | PANTHENOL | 0.200 |
|  | GLYCERIN | 5.000 |
|  | SODIUM PCA | 0.500 |
|  | TETRASODIUM EDTA | 0.100 |
|  | ALLANTOIN | 0.250 |
| B | PROMULGEN D | 3.000 |
|  | CETYL ALCOHOL | 2.000 |
|  | STEARIC ACID | 2.000 |
|  | LIPONATE G C | 5.000 |
|  | CYCLOM + ETHICONE | 3.500 |
|  | RICE BRAN OIL | 0.100 |
|  | AVOCADO OIL | 0.100 |
|  | DIMETHICONE 47V20 | 1.500 |
|  | OLIVE OIL | 3.500 |
|  | VITAMIN E | 0.050 |

| | | |
|---|---|---|
| C | SIMULGEL NS | 2.000 |
| D | OPTIPHEN PLUS | 1.000 |
| E | GRAPE SEED EXTRACT | 0.100 |
| | VITABERRY | 0.100 |
| | QUERCETIN | 0.100 |
| | GOJI BERRY EXTRACT POWDER | 0.250 |
| | COFFEE CHERRY EXTRACT POWDER | 10.000 |
| F | VITAMIN A | 0.050 |
| | VITAMIN C | 0.010 |
| | HYASOL | 1.500 |
| G | BIOTIN | 0.100 |
| H | OPC PINE BARK | 0.500 |
| | ACAI EXTRACT | 0.100 |
| | GUARANA EXTRACT | 1.000 |
| | GREEN TEA EXTRACT | 0.100 |
| | LICORICE EXTRACT | 0.100 |
| | CUCUMBER EXTRACT | 0.100 |
| | CHAMOMILE EXTRACT | 0.100 |
| I | TEA 99% | 0.400 |
| J | GRAPEFRUIT OIL #1854 | 0.100 |
| | ORANGE OIL #1085 | 0.100 |
| | AROMATIC POMEGRANATE EXTRACT #H2580 | 0.100 |
| | | 100.00 |

| Attribute | Specs (Range) | ACTUAL |
|---|---|---|
| pH | 4.0-5.0 | |
| Odor | CHARACTERISTIC | |
| Color | .BROWN | |
| Viscosity | T/C 28,000-40,000cp5rpm | |

The above formulation is processed by heating phase A to 70° C. in a first main vessel. Phase B is heated in a separate vessel to 70° C., and phases A and B are homogenized together to form a main batch. Phase C is homogenized with the main batch, and the resulting mixture is cooled to room temperature. Phase D is added to the cooled mixture followed by phase E to give a combined mixture. Phase F is premixed and added to the combined mixture, followed by phases G, H, I and J.

Example 2

Repair & Replenish Night Crème

| Phase | Constituents | Wt. Percent |
|---|---|---|
| A | STABILIZED AV GEL | 45.390 |
| | XANTHAN GUM | 0.300 |
| | CARBOPOL 940 2% | 10.000 |
| | HYDROLITE-5 | 2.000 |
| | PANTHENOL | 0.200 |
| | GLYCERN | 5.000 |
| | SODIUM PCA | 0.500 |
| | TETRASODIUM EDTA | 0.100 |
| | ALLANTOIN | 0.250 |
| B | PROMULGEN D | 3.000 |
| | CETYL ALCOHOL | 2.000 |
| | STEARIC ACID | 2.000 |
| | LIPONATE GC | 5.000 |
| | CYCLOMETHICONE | 3.500 |
| | RICE BRAN OIL | 0.100 |
| | AVOCADO OIL | 0.100 |
| | DIMETHICONE 47V20 | 1.500 |
| | OLIVE OIL | 3.500 |
| | VITAMIN E | 0.050 |
| C | SIMULGEL NS | 1.500 |
| D | OPTIPHEN PLUS | 1.000 |
| E | GRAPE SEED EXTRACT | 0.100 |
| | VITABERRY PLUS | 0.100 |
| | QUERCETIN POWDER | 0.100 |
| | GOJI BERRY EXTRACT POWDER | 0.250 |
| | GREEN COFFEE EXTRACT POWDER | 5.000 |
| F | VITAMIN A | 0.050 |
| | VITAMIN C | 0.010 |
| | HYASOL | 1.500 |
| G | BIOTIN | 0.100 |
| H | ACAI EXTRACT | 0.100 |
| | OPC PINE BARK | 0.500 |
| | CHAMOMILE EXTRACT | 0.250 |
| | GUARANA EXTRACT | 2.000 |
| | GREEN TEA EXTRACT | 0.100 |
| | LICORICE EXTRACT | 0.100 |
| | CUCUMBER EXTRACT | 0.100 |
| I | ORANGE OIL | 0.750 |
| | GRAPEFRUIT OIL | 0.750 |
| | AROMATIC POMEGRANATE EXTRACT #2580 | 0.750 |
| J | TEA 99% | 0.400 |
| | | 100.00 |

| Attribute | Specs (Range) | ACTUAL |
|---|---|---|
| pH | 5.0-6.0 | |
| Odor | CHARACTERISTIC | |
| Color | BROWN | |
| Viscosity | T/C 40,000-55,000cp5rpm | |

The above formulation is processed by heating phase A to 70° C. in a first main vessel. Phase B is heated in a separate vessel to 70° C., and phases A and B are homogenized together to form a main batch. Phase C is homogenized with the main batch, and the resulting mixture is cooled to room temperature. Phase D is added to the cooled mixture. Phase E is premixed and added to the cooled mixture, followed by phases F, G, H, I and J.

Example 3

Protect & Rejuvinate Day Lotion

| Phase | Constituents | Wt. Percent |
|---|---|---|
| A | STABILIZED AV GEL | 51.990 |
| | XANTHAN GUM | 0.300 |
| | CARBOPOL 940 2% | 10.000 |
| | HYDROLITE-5 | 2.000 |
| | PANTHENOL | 0.200 |
| | GLYCERN | 5.000 |
| | SODIUM PCA | 0.500 |
| | TETRASODIUM EDTA | 0.100 |
| | ALLANTOIN | 0.250 |
| B | PROMULGEN D | 3.000 |
| | CETYL ALCOHOL | 2.000 |
| | STEARIC ACID | 2.000 |
| | LIPONATE GC | 5.000 |
| | CYCLOMETHICONE | 3.500 |
| | RICE BRAN OIL | 0.100 |
| | AVOCADO OIL | 0.100 |
| | DIMETHICONE 47V20 | 1.500 |
| | OLIVE OIL | 3.500 |
| | VITAMIN E | 0.050 |
| C | SIMULGEL NS | 1.000 |
| D | OPTIPHEN PLUS | 1.000 |
| E | GRAPE SEED EXTRACT | 0.100 |
| | VITABERRY PLUS | 0.100 |
| | QUERCETIN POWDER | 0.100 |
| | GOJI BERRY EXTRACT POWDER | 0.100 |
| | GREEN COFFEE EXTRACT POWDER | 1.000 |
| F | VITAMIN A | 0.050 |
| | VITAMIN C | 0.010 |
| | HYASOL | 1.500 |

-continued

| | | |
|---|---|---|
| G | BIOTIN | 0.100 |
| H | ACAI EXTRACT | 0.100 |
| | OPC PINE BARK | 0.500 |
| | CHAMOMILE EXTRACT | 0.250 |
| | GUARANA EXTRACT | 2.000 |
| | GREEN TEA EXTRACT | 0.100 |
| | LICORICE EXTRACT | 0.100 |
| | CUCUMBER EXTRACT | 0.100 |
| I | ORANGE OIL | 0.100 |
| | GRAPEFRUIT OIL | 0.100 |
| | AROMATIC POMEGRANATE EXTRACT #2580 | 0.100 |
| J | TEA 99% | 0.400 |
| | | 100.00 |

| Attribute | Specs (Range) | ACTUAL |
|---|---|---|
| pH | 4.75-5.75 | |
| Odor | CHARACTERSTIC | |
| Color | BROWN | |
| Viscosity | T/C 38,000-48,000cp5rpm | |

The above formulation is processed by heating phase A to 70° C. in a first main vessel. Phase B is heated in a separate vessel to 70° C., and phases A and B are homogenized together to form a main batch. Phase C is homogenized with the main batch, and the resulting mixture is cooled to room temperature. Phase D is added to the cooled mixture. Phase E is premixed and added to the cooled mixture, followed by phases F, G, H, I and J.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An antioxidant skin care composition comprising in w %: stabilized AV gel 38-44, xanthan gum 0.1-0.5, cross-linked polyacrylate polymer (2%) 5-15, pentylene glycol 1-5, panthenol 0.1-0.5, glycerin 2-8, sodium PCA 0.2-0.9, tetrasodium EDTA 0.05-0.5, allantoin 0.1-0.5, ethoxylated cetearyl alcohol compounded with cetaryl alcohol 1-5, cetyl alcohol 1-5, stearic acid 1-5, caprylic/capric triglyceride 2-10, cyclomethicone 1-5, rice bran oil 0.05-0.5, avocado oil 0.05-0.5, polydimethylsiloxane 1-4, olive oil 1-5, vitamin E 0.01-0.1, hydroxyethylacrylate/sodium acryloyldimethyl taurate copolymer & squalane & polyoxyethylene (20) sorbitan monostearate 1-5, phenoxyethanol and caprylyl glycol and sorbic acid 0.1-5, grape seed extract 0.05-0.5, antioxidant blend of whole fruit powders and extracts combining wild blueberry, cranberry, raspberry, strawberry, prune, cherry, wild bilberry and grape 0.05-0.5, quercetin 0.05-0.5, goji berry extract powder 0.1-0.5, coffee cherry extract powder or green coffee extract powder 5-15, vitamin A 0.01-0.1, vitamin C 0.05-0.1, hyasol 1-5, biotin 0.05-0.5, OPC pine bark 0.1-1.0, ACAI extract 0.05-0.5, guarana extract 0.5-5, green tea extract 0.05-0.5, licorice extract 0.05-0.5, cucumber extract 0.05-0.5, chamomile extract 0.05-0.5, tea 99% 0.01-1, grapefruit oil #1854 0.05-0.5, orange oil #1085 0.05-0.5, aromatic pomegranate extract #H2580 0.05-0.5, to a total of 100.00.

2. An antioxidant skin care composition comprising the following constituents:

| Constituents | Wt. Percent |
|---|---|
| STABILIZED AV GEL | 42.990 |
| XANTHAN GUM | 0.300 |
| CROSS-LINKED POLYACRYLATE POLYMER (2%) | 10.000 |
| PENTYLENE GLYCOL | 2.000 |
| PANTHENOL | 0.200 |
| GLYCERN | 5.000 |
| SODIUM PCA | 0.500 |
| TETRASODIUM EDTA | 0.100 |
| ALLANTOIN | 0.250 |
| ETHOXYLATED CETEARYL ALCOHOL COMPOUNDED WITH CETARYL ALCOHOL | 3.000 |
| CETYL ALCOHOL | 2.000 |
| STEARIC ACID | 2.000 |
| CAPRYLIC/CAPRIC TRIGLYCERIDE | 5.000 |
| CYCLOMETHICONE | 3.500 |
| RICE BRAN OIL | 0.100 |
| AVOCADO OIL | 0.100 |
| POLYDIMETHYISILOXANE | 1.500 |
| OLIVE OIL | 3.500 |
| VITAMIN E | 0.050 |
| HYDROXYETHYLACRYLATE/SODIUM ACRYLOYLDIMETHYL TAURATE COPOLYMER & SQUALANE & POLYOXYETHYLENE (20) SORBITAN MONOSTEARATE | 2.000 |
| PHENOXYETHANOL AND CAPRYIYL GLYCOL AND SORBIC ACID | 1.000 |
| GRAPE SEED EXTRACT | 0.100 |
| ANTIOXIDANT BLEND OF WHOLE FRUIT POWDERS AND EXTRACTS COMBINING WILD BLUEBERRY, CRANBERRY, RASPBERRY, STRAWBERRY, PRUNE, CHERRY, WILD BILBERRY AND GRAPE | 0.100 |
| QUERCETIN | 0.100 |
| GOB BERRY EXTRACT POWDER | 0.250 |
| COFFEE CHERRY EXTRACT POWDER | 10.000 |
| VITAMIN A | 0.050 |
| VITAMIN C | 0.010 |
| HYASOL | 1.500 |
| BIOTIN | 0.100 |
| OPC PINE BARK | 0.500 |
| ACAI EXTRACT | 0.100 |
| GUARANA EXTRACT | 1.000 |
| GREEN TEA EXTRACT | 0.100 |
| LICORICE EXTRACT | 0.100 |
| CUCUMBER EXTRACT | 0.100 |
| CHAMOMILE EXTRACT | 0.100 |
| TEA 99% | 0.400 |
| GRAPEFRUIT OIL #1854 | 0.100 |
| ORANGE OIL #1085 | 0.100 |
| AROMATIC POMEGRANATE EXTRACT #H2580 | 0.100 |
| | 100.00. |

3. An antioxidant skin care composition comprising the following constituents:

| Constituents | Wt. Percent |
|---|---|
| STABILIZED AV GEL | 45.390 |
| XANTHAN GUM | 0.300 |
| CROSS-LINKED POLYACRYLATE POLYMER (2%) | 10.000 |
| PENTYLENE GLYCOL | 2.000 |
| PANTHENOL | 0.200 |
| GLYCERN | 5.000 |
| SODIUM PCA | 0.500 |
| TETRASODIUM EDTA | 0.100 |
| ALLANTOIN | 0.250 |
| ETHOXYLATED CETEARYL ALCOHOL COMPOUNDED WITH CETARYL ALCOHOL | 3.000 |
| CETYL ALCOHOL | 2.000 |
| STEARIC ACID | 2.000 |
| CAPRYLIC/CAPRIC TRIGLYCERIDE | 5.000 |

-continued

| Constituents | Wt. Percent |
|---|---|
| CYCLOMETHICONE | 3.500 |
| RICE BRAN OIL | 0.100 |
| AVOCADO OIL | 0.100 |
| POLYDIMETHYISILOXANE | 1.500 |
| OLIVE OIL | 3.500 |
| VITAMIN E | 0.050 |
| HYDROXYETHYLACRYLATE/SODIUM ACRYLOYLDIMETHYL TAURATE COPOLYMER & SQUALANE & POLYOXYETHYLENE (20) SORBITAN MONOSTEARATE | 1.500 |
| HYDROXYETHYLACRYLATE/SODIUM PHENOXYETHANOL AND CAPRYLYL GLYCOL AND SORBIC ACID | 1.000 |
| GRAPE SEED EXTRACT | 0.100 |
| ANTIOXIDANT BLEND OF WHOLE FRUIT POWDERS AND EXTRACTS COMBINING WILD BLUEBERRY, CRANBERRY, RASPBERRY, STRAWBERRY, PRUNE, CHERRY, WILD BILBERRY AND GRAPE | 0.100 |
| QUERCETIN POWDER | 0.100 |
| GOJI BERRY EXTRACT POWDER | 0.250 |
| GREEN COFFEE EXTRACT POWDER | 5.000 |
| VITAMIN A | 0.050 |
| VITAMIN C | 0.010 |
| HYASOL | 1.500 |
| BIOTIN | 0.100 |
| ACAI EXTRACT | 0.100 |
| OPC PINE BARK | 0.500 |
| CHAMOMILE EXTRACT | 0.250 |
| GUARANA EXTRACT | 2.000 |
| GREEN TEA EXTRACT | 0.100 |
| LICORICE EXTRACT | 0.100 |
| CUCUMBER EXTRACT | 0.100 |
| ORANGE OIL | 0.750 |
| GRAPEFRUIT OIL | 0.750 |
| AROMATIC POMEGRANATE EXTRACT #2580 | 0.750 |
| TEA 99% | 0.400 |
| | 100.00. |

4. An antioxidant skin care composition comprising the following constituents:

| Constituents | Wt. Percent |
|---|---|
| STABILIZED AV GEL | 51.990 |
| XANTHAN GUM | 0.300 |
| CROSS-LINKED POLYACRYLATE POLYMER 2% | 10.000 |

-continued

| Constituents | Wt. Percent |
|---|---|
| HYDROLITE-5 | 2.000 |
| PANTHENOL | 0.200 |
| GLYCERN | 5.000 |
| SODIUM PCA | 0.500 |
| TETRASODIUM EDTA | 0.100 |
| ALLANTOIN | 0.250 |
| ETHOXYLATED CETEARYL ALCOHOL COMPOUNDED WITH CETARYL ALCOHOL | 3.000 |
| CETYL ALCOHOL | 2.000 |
| STEARIC ACID | 2.000 |
| CAPRYLIC/CAPRIC TRIGLYCERIDE | 5.000 |
| CYCLOMETHICONE | 3.500 |
| RICE BRAN OIL | 0.100 |
| AVOCADO OIL | 0.100 |
| POLYDIMETHYISILOXANE | 1.500 |
| OLIVE OIL | 3.500 |
| VITAMIN E | 0.050 |
| HYDROXYETHYLACRYLATE/SODIUM ACRYLOYLDIMETHYL TAURATE COPOLYMER & SQUALANE & POLYOXYETHYLENE (20) SORBITAN MONOSTEARATE | 1.000 |
| PHENOXYETHANOL AND CAPRYLYL GLYCOL AND SORBIC ACID | 1.000 |
| GRAPE SEED EXTRACT | 0.100 |
| ANTIOXIDANT BLEND OF WHOLE FRUIT POWDERS AND EXTRACTS COMBINING WILD BLUEBERRY, CRANBERRY, RASPBERRY, STRAWBERRY, PRUNE, CHERRY, WILD BILBERRY AND GRAPE | 0.100 |
| QUERCETIN POWDER | 0.100 |
| GOJI BERRY EXTRACT POWDER | 0.100 |
| GREEN COFFEE EXTRACT POWDER | 1.000 |
| VITAMIN A | 0.050 |
| VITAMIN C | 0.010 |
| HYASOL | 1.500 |
| BIOTIN | 0.100 |
| ACAI EXTRACT | 0.100 |
| OPC PINE BARK | 0.500 |
| CHAMOMILE EXTRACT | 0.250 |
| GUARANA EXTRACT | 2.000 |
| GREEN TEA EXTRACT | 0.100 |
| LICORICE EXTRACT | 0.100 |
| CUCUMBER EXTRACT | 0.100 |
| ORANGE OIL | 0.100 |
| GRAPEFRUIT OIL | 0.100 |
| AROMATIC POMEGRANATE EXTRACT #2580 | 0.100 |
| TEA 99% | 0.400 |
| | 100.00. |

\* \* \* \* \*